(12) United States Patent
Luo et al.

(10) Patent No.: US 9,228,888 B2
(45) Date of Patent: Jan. 5, 2016

(54) SENSOR POSITIONING WITH NON-DISPERSIVE GUIDED WAVES FOR PIPELINE CORROSION MONITORING

(71) Applicant: General Electric Company, Schenectady, NY (US)

(72) Inventors: Wei Luo, Chandler, AZ (US); James Norman Barshinger, State Collegte, PA (US); Debasish Mishra, Bangalore (IN); Anusha Rammohan, Karnataka (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 332 days.

(21) Appl. No.: 13/747,522

(22) Filed: Jan. 23, 2013

(65) Prior Publication Data

US 2014/0202249 A1    Jul. 24, 2014

(51) Int. Cl.
*G01N 29/26* (2006.01)
*G01H 5/00* (2006.01)
*G01N 29/04* (2006.01)
*G01N 29/22* (2006.01)
*G01N 29/07* (2006.01)

(52) U.S. Cl.
CPC .............. *G01H 5/00* (2013.01); *G01N 29/041* (2013.01); *G01N 29/07* (2013.01); *G01N 29/223* (2013.01); *G01N 2291/0425* (2013.01); *G01N 2291/106* (2013.01); *G01N 2291/2634* (2013.01); *Y10T 29/49764* (2015.01)

(58) Field of Classification Search
CPC .................................................... G01N 29/223
USPC .......................................................... 73/622
See application file for complete search history.

(56) References Cited

U.S. PATENT DOCUMENTS

| 4,004,461 A * | 1/1977 | Lynnworth ................ 73/861.27 |
| 4,080,837 A * | 3/1978 | Alexander et al. ........... 73/61.45 |
| 4,605,924 A * | 8/1986 | Marini et al. .................. 340/683 |

(Continued)

FOREIGN PATENT DOCUMENTS

| EP | 2439527 A1 | 4/2012 |
| GB | 2403009 A | 12/2004 |

(Continued)

OTHER PUBLICATIONS

Hoe Woong Kim et al: "Shear-horizontal wave-based pipe damage inspection by arrays of segmented magnetostrictive patches", IEEE Transactions on Ultrasonics, Ferroelectrics and Frequency Control, IEEE, US, part 58, No. 12, Dec. 2011 pp. 2689-2698.

(Continued)

*Primary Examiner* — John Chapman, Jr.
(74) *Attorney, Agent, or Firm* — Cooper Legal Group, LLC

(57) ABSTRACT

An ultrasonic sensor assembly for testing a pipe includes a first and second transducer rings attached to the pipe and spaced apart along a length of the pipe. The first transducer ring includes a plurality of transmitters for transmitting a wave, such as a non-dispersive guided wave. The first transducer ring transmits the wave along the pipe. The second transducer ring includes a plurality of receivers for receiving the wave. A relative position of the first transducer ring with respect to a circumferential position of the second transducer ring is determined based on characteristics of the wave received by the second transducer ring. A method of positioning the ultrasonic sensor assembly on the pipe is also provided.

20 Claims, 4 Drawing Sheets

(56) References Cited

U.S. PATENT DOCUMENTS

| | | | | |
|---|---|---|---|---|
| 5,040,415 | A | * | 8/1991 | Barkhoudarian ............... 73/198 |
| 5,214,251 | A | * | 5/1993 | Orban et al. ................... 181/102 |
| 5,359,897 | A | * | 11/1994 | Hamstead et al. .............. 73/597 |
| 6,568,271 | B2 | * | 5/2003 | Shah et al. ...................... 73/599 |
| 7,624,651 | B2 | * | 12/2009 | Fernald et al. ............. 73/861.27 |

FOREIGN PATENT DOCUMENTS

| | | | |
|---|---|---|---|
| GB | 2508515 | A | 6/2014 |
| JP | 2007003537 | A | 1/2007 |

OTHER PUBLICATIONS

Hoe Woong Kim et al: "Circumferential phased array of shear-horizontal wave magnetostrictive patch transducers for pipe inspection", Ultrasonics, part 53, No. 2, Aug. 7, 2012 pp. 423-431.

Unofficial translation of NL Search Report and Written Opinion issued in connection with corresponding NL Patent Application No. 2012117 dated Jun. 27, 2014.

GB Search Report issued in connection with corresponding GB Application No. 1400874.2 on Jul. 2, 2014.

\* cited by examiner

SENSOR POSITIONING WITH NON-DISPERSIVE GUIDED WAVES FOR PIPELINE CORROSION MONITORING

BACKGROUND OF THE INVENTION

1. Field of the Invention

The present invention relates generally to ultrasonic sensor assemblies, and more particularly, to aligning an ultrasonic sensor assembly on a pipe.

1. Discussion of the Prior Art

Ultrasonic sensor assemblies are known and used in many different applications. Ultrasonic sensor assemblies are used, for example, to inspect a pipe and detect/identify at least one characteristic of the pipe, such as corrosion, voids, inclusions, length, thickness, etc. To accurately determine the location of these characteristics of the pipe, a relative position of a first transducer ring with respect to a second transducer ring should be known. In the past, the first transducer ring would be precisely longitudinally aligned with the second transducer ring, such that circumferential locations of transmitters in the first transducer ring would match circumferential locations of receivers in the second transducer ring. Providing precise longitudinal alignment could be difficult and time consuming. Further, alignment tools (e.g., mechanical tools, optical/laser tools, software based tools, etc.) were used to assist in longitudinal alignment.

Accordingly, it would be beneficial to provide an ultrasonic sensor assembly that allows for the transducer rings to be arbitrarily installed on the pipe. Further, it would be beneficial to provide this arbitrary installation of the transducer rings without the need for alignment tools.

BRIEF DESCRIPTION OF THE INVENTION

The following presents a simplified summary of the invention in order to provide a basic understanding of some example aspects of the invention. This summary is not an extensive overview of the invention. Moreover, this summary is not intended to identify critical elements of the invention nor delineate the scope of the invention. The sole purpose of the summary is to present some concepts of the invention in simplified form as a prelude to the more detailed description that is presented later.

In accordance with one aspect, an ultrasonic sensor assembly for testing a pipe is provided. The ultrasonic sensor assembly includes a first transducer ring attached to the pipe and a second transducer ring attached to the pipe and spaced from the first transducer ring along a length of the pipe. The first transducer ring transmits a wave along the pipe that is received by the second transducer ring. A relative position of the first transducer ring with respect to a circumferential position of the second transducer ring is determined based on characteristics of the wave received by the second transducer ring.

In accordance with another aspect, an ultrasonic sensor assembly for testing a pipe is provided. The ultrasonic sensor assembly includes a first transducer ring attached to the pipe. The first transducer ring includes a plurality of transmitters for transmitting a plurality of non-dispersive guided waves along the pipe. The ultrasonic sensor assembly includes a second transducer ring spaced apart from the first transducer ring and attached to the pipe. The second transducer ring includes a plurality of receivers for receiving the non-dispersive guided waves from the first transducer ring. A relative position of the first transducer ring with respect to a circumferential position the second transducer ring is determined based on a comparison of a time of flight for the non-dispersive guided waves received by the receivers in the second transducer ring.

In accordance with another aspect, a method of positioning an ultrasonic sensor assembly on a pipe is provided. The method includes the steps of attaching a first transducer ring to the pipe. The method further includes the step of attaching a second transducer ring to the pipe spaced apart from the first transducer ring. The method includes the step of transmitting a wave along the pipe from the first transducer ring to the second transducer ring. The method includes the step of determining the relative position of the first transducer ring with respect to a circumferential position of the second transducer ring based on characteristics of the wave received by the second transducer ring.

BRIEF DESCRIPTION OF THE DRAWINGS

The foregoing and other aspects of the present invention will become apparent to those skilled in the art to which the present invention relates upon reading the following description with reference to the accompanying drawings, in which.

DETAILED DESCRIPTION OF THE INVENTION

Figure 1:
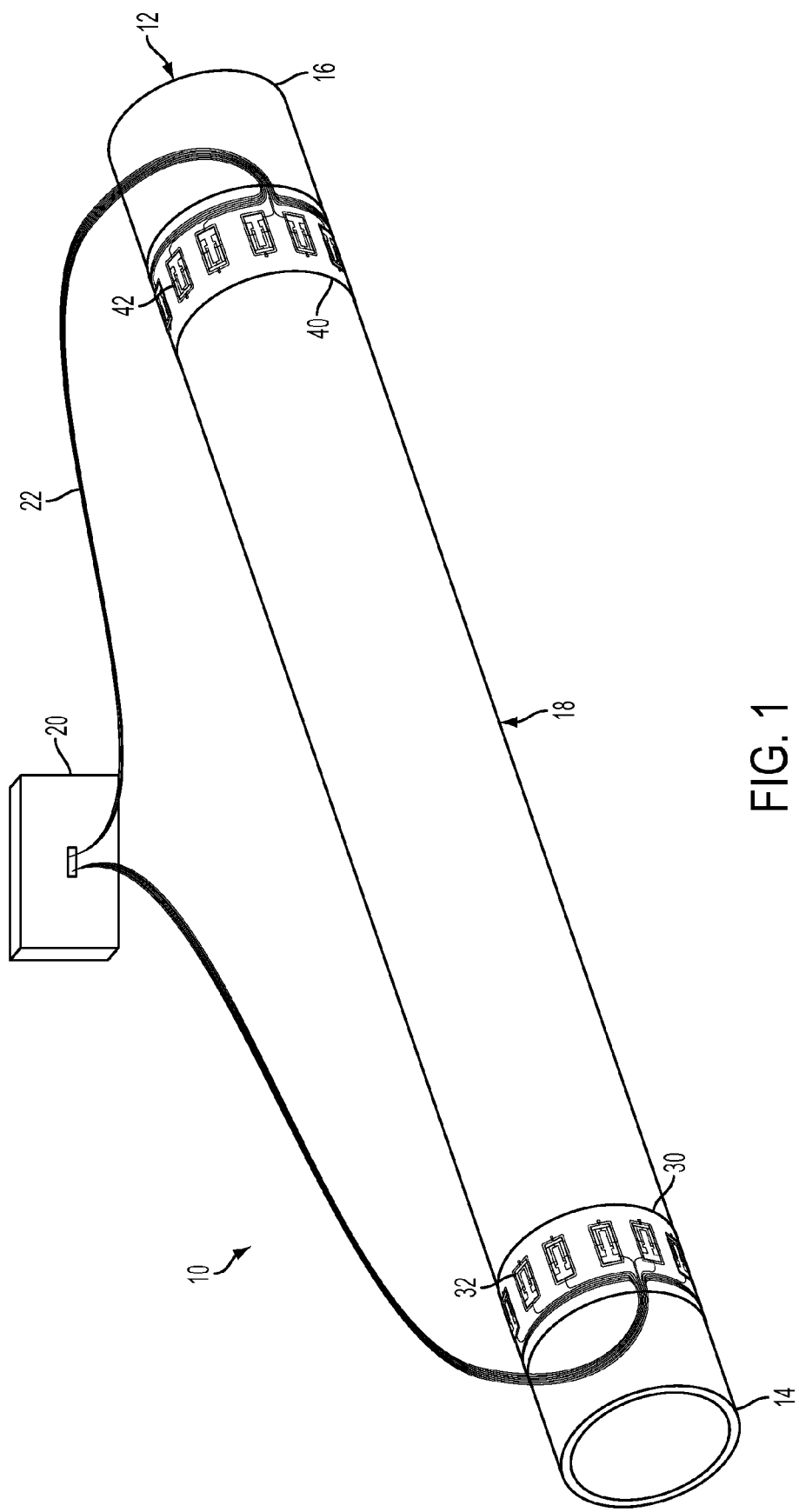
FIG. 1 is a schematic, perspective view of an example ultrasonic sensor assembly being used with a pipe in accordance with an aspect of the present invention.

Example embodiment(s) that incorporate one or more aspects of the present invention are described and illustrated in the drawings. These illustrated examples are not intended to be a limitation on the present invention. For example, one or more aspects of the present invention can be utilized in other embodiments and even other types of devices. Moreover, certain terminology is used herein for convenience only and is not to be taken as a limitation on the present invention. Still further, in the drawings, the same reference numerals are employed for designating the same elements.

FIG. 1 illustrates a perspective view of an example ultrasonic sensor assembly 10 according to one aspect of the invention. In short summary, the ultrasonic sensor assembly 10 includes a controller 20 in operative association with a first transducer ring 30 and a second transducer ring 40. The first and second transducer rings 30, 40 can transmit ultrasonic waves into a pipe 12 for testing the pipe 12, including sensing and detecting a characteristic (e.g., corrosion, thickness, voids, inclusions, etc.) of the pipe 12. To provide improved sensing of the pipe 12, a relative position of the first transducer ring 30 with respect to the second transducer ring 40 is determined based on analyzing one or more waves 50 (see FIG. 2, waves schematically represented as arrowheads) received by the second transducer ring 40 from the first transducer ring 30.

The pipe 12 is shown to include a tubular pipe having a generally cylindrical shape extending between a first end 14 and an opposing second end 16. The pipe 12 can include a non-solid body (e.g., hollow body) or may be solid. It is to be appreciated that the pipe 12 is somewhat generically/schematically depicted in FIGS. 1 and 2 for ease of illustration. Indeed, the pipe 12 is not limited to the pipe extending along a linear axis, and may include bends, undulations, curves, or the like. The pipe 12 has an outer surface 18 forming a generally cylindrical shape. In further examples, the pipe 12 includes other non-cylindrical shapes and sizes. For example, the pipe 12 could have a non-circular cross-sectional shape, such as by having a square or rectangular cross-section. Still further, the pipe 12 may include a tubular shape, conical shape, or the like. The pipe is not limited to pipes, but instead, could include walls, planar or non-planar surfaces, etc. The pipe 12 could be used in a number of applications, including pipeline corrosion monitoring. As such, the pipe 12 shown in FIG. 1 comprises only one possible example of the pipe.

Turning to the controller 20, the controller is somewhat generically/schematically depicted. In general, the controller 20 can include any number of different configurations. In one example, the controller 20 is operatively attached to the first transducer ring 30 and second transducer ring 40 by means of a wire 22. In further examples, however, the controller 20 could be in wireless communication with the first and second transducer rings 30, 40. The controller 20 can send and receive information (e.g., data, control instructions, etc.) from the first transducer ring 30 through the wire 22 (or wirelessly). This information can be related to characteristics of the pipe 12 (e.g., corrosion, wall thickness, voids, inclusions, etc.), characteristics of the waves 50 transmitted and/or received by the first and second transducer rings 30, 40, or the like. The controller 20 can include circuits, processors, running programs, memories, computers, power supplies, ultrasound contents, or the like. In further examples, the controller 20 includes a user interface, display, and/or other devices for allowing a user to control the ultrasonic sensor assembly 10.

Figure 2:
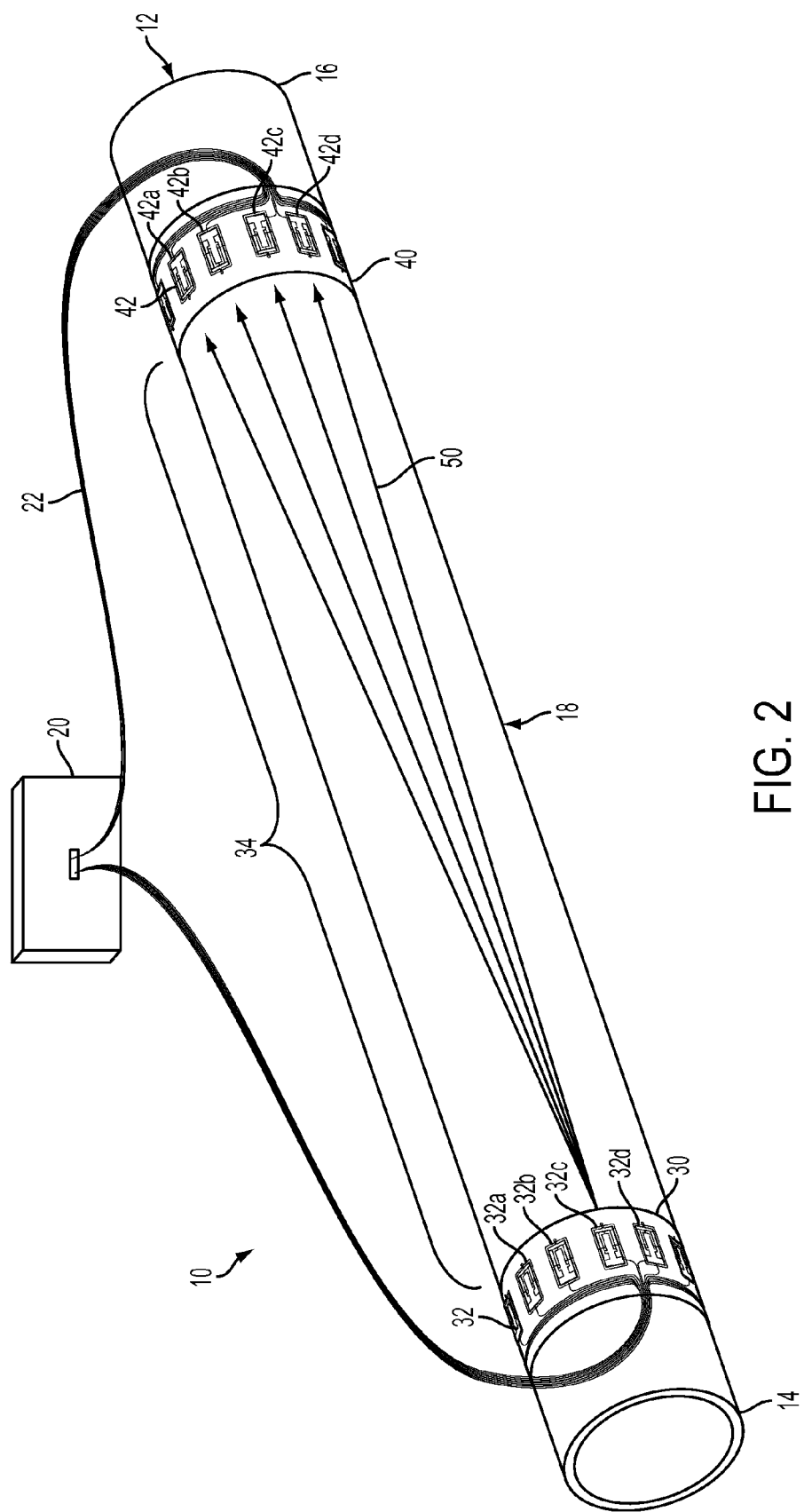
FIG. 2 is a schematic, perspective view of the example ultrasonic sensor assembly similar to FIG. 1 with waves being transmitted from a first transducer ring to a second transducer ring.

Turning now to FIG. 2, the ultrasonic sensor assembly 10 includes the first transducer ring 30. The first transducer ring 30 can include a size and shape that substantially matches a size and shape of the pipe 12. For example, the first transducer ring 30 can be attached (e.g., temporarily or permanently) to the pipe 12, such that the first transducer ring 30 wraps around the outer surface 18. In the shown example, the first transducer ring 30 has a generally circular shape with a diameter that is slightly larger than a diameter of the pipe 12. As such, the first transducer ring 30 is in contact with the outer surface 18. Of course, in further examples, the first transducer ring 30 is not limited to having the circular cross-sectional shape, and could include nearly any cross-sectional size and shape that matches the cross-sectional size and shape of the pipe 12. In another example, the first transducer ring 30 is formed from a flexible material that can be wrapped around the pipe 12.

The first transducer ring 30 is shown to be positioned near the first end 14 of the pipe 12. In further examples, however, the first transducer ring 30 is not so limited to such a position, and could be arranged at nearly any location along the length of the pipe 12. For example, the first transducer ring 30 could be closer or farther from the first end 14, adjacent the second end 16, or the like.

The first transducer ring 30 includes one or more transmitters 32. The transmitters 32 are supported (e.g., fixed) to the first transducer ring 30, such as being supported by a backing material or the like. The transmitters 32 are somewhat generically/schematically shown, as it is to be appreciated that the transmitters 32 include nearly any size, shape, and configuration. The transmitters 32 are provided to extend around the first transducer ring 30 and in contact with the outer surface 18. The transmitters 32 can be positioned to extend substantially 360° around the outer surface 18 of the pipe 12.

The first transducer ring 30 can be provided with any number of transmitters 32. Further, the transmitters 32 can be arranged to be closer together or farther apart than as shown. In the shown example, the transmitters 32 include a first transmitter 32a, a second transmitter 32b, a third transmitter 32c, and a fourth transmitter 32d. While only these four transmitters are labeled in FIG. 2, it is understood that the first transducer ring 30 is not limited to including the four transmitters. The first transducer ring 30 could likewise include a fifth transmitter, sixth transmitter, etc. Indeed, other transmitters 32 are included within the first transducer ring 30 but are obstructed from view.

Each of the transmitters 32 is capable of transmitting (e.g., sending, conveying, etc.) one or more of the waves 50, including a pulse, energy, and/or other impulses, along the pipe 12. It is to be appreciated that the waves 50 are somewhat generically/schematically depicted as arrows for ease of illustration. The waves 50 can propagate along an inspection region 34 through the pipe 12 from the first transducer ring 30. In one example, the waves 50 propagate longitudinally along the pipe 12 (e.g., longitudinal guided wave mode). In other examples, the waves 50 include torsional (shear) and flexural modes in addition to the longitudinal mode. The transmitters 32 can transmit a number of different types of waves 50. In one possible example, the waves 50 are used to detect characteristics within the pipe 12 (e.g., corrosion, thickness, cracks, voids, inclusions, etc.). In another example, the transmitters 32 each transmit non-dispersive guided waves. As is generally known, non-dispersive guided waves have a generally constant velocity traveling through a given medium (e.g., pipe 12 in the shown example) regardless of the presence or absence of corrosion, thickness variations, cracks, or the like.

The ultrasonic sensor assembly 10 further includes the second transducer ring 40 spaced apart from the first transducer ring 30 along a length of the pipe 12. The second transducer ring 40 includes a size and shape that substantially matches a size and shape of the pipe 12. For example, the second transducer ring 40 is attached to the pipe 12 (e.g., temporarily or permanently), such that the second transducer ring 40 wraps around the outer surface 18. In the shown example, the second transducer ring 40 has a generally circular shape with a diameter that is slightly larger than a diameter of the pipe 12. As such, the second transducer ring 40 is in contact with the outer surface 18. Of course, in further examples, the second transducer ring 40 is not limited to having the circular cross-sectional shape, and could include nearly any cross-sectional size and shape that matches the cross-sectional size and shape of the pipe 12.

The second transducer ring 40 is shown to be positioned near the second end 16 of the pipe 12. In further examples, however, the second transducer ring 40 is not so limited to such a position, and could be arranged at nearly any location along the length of the pipe 12. For example, the second transducer ring 40 could be closer or farther from the second end 16, adjacent the first end 14, or the like. Indeed, the positions of the first transducer ring 30 and second transducer ring 40 could be switched, such that the first transducer ring 30 is closer to the second end 16 while the second transducer ring 40 is closer to the first end 14.

The second transducer ring 40 includes one or more receivers 42. The receivers 42 are supported (e.g., fixed) to the second transducer ring 40, such as being supported by a backing material or the like. The receivers 42 are somewhat generically/schematically shown, as it is to be appreciated that the receivers 42 include nearly any size, shape, and configuration. The receivers 42 are provided to extend around the second transducer ring 40 and in contact with the outer surface 18. The receivers 42 can be positioned to extend substantially 360° around the outer surface 18 of the pipe 12.

The second transducer ring 40 can be provided with any number of receivers 42. Further, the receivers 42 can be arranged to be closer together or farther apart than as shown. In the shown example, the receivers 42 include a first receiver 42a, a second receiver 42b, a third receiver 42c, and a fourth receiver 42d. While only these four receivers are labeled in FIG. 2, it is understood that the second transducer ring 40 is not limited to including the four receivers. Rather, the second transducer ring 40 could likewise include a fifth receiver, sixth receiver, etc.

Each of the receivers 42 is capable of receiving the waves 50 (e.g., pulse, energy, other impulses, etc.) from the transmitters 32 of the first transducer ring 30. In one example, the waves 50 received by the receivers 42 can be inspected, such as with the controller 20, to detect the characteristics of the pipe 12. In particular, features of the waves 50 including a time of flight, amplitude, or the like are analyzed to detect the characteristics. To provide more accurate determination of these characteristics, the waves 50 can first be analyzed to detect the relative position of the first transducer ring 30 with respect to a circumferential position of the second transducer ring 40.

Figure 3:
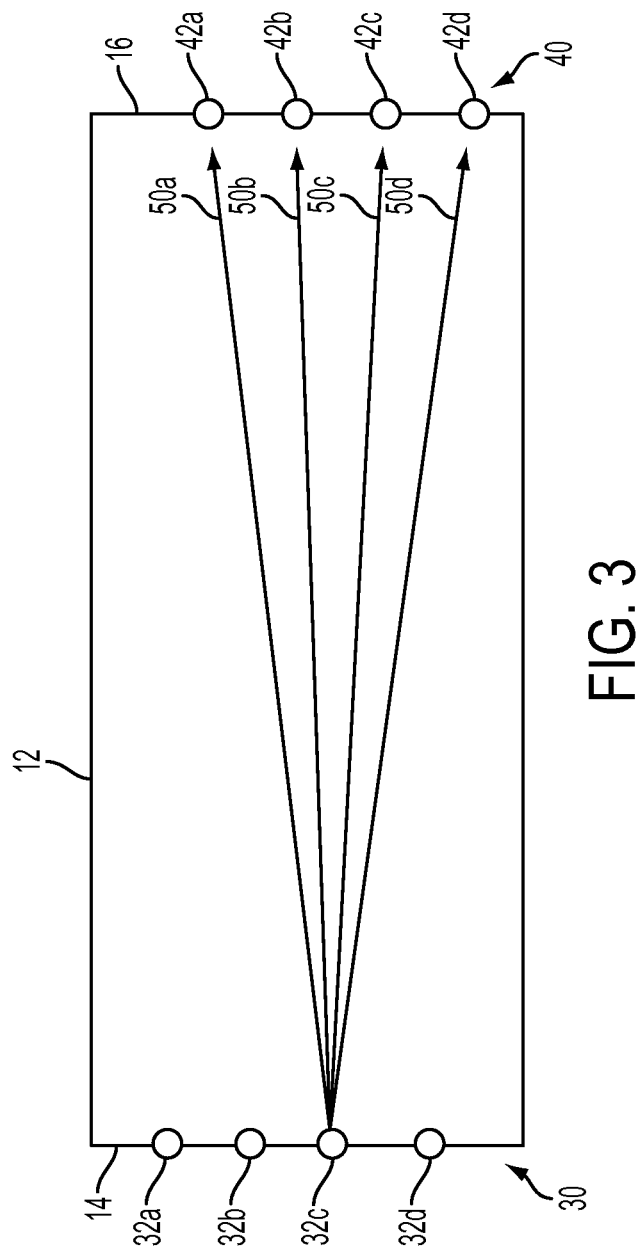
FIG. 3 is an unwrapped planar view of the ultrasonic sensor assembly and the pipe.

Turning now to FIG. 3, the operation of determining the relative position of the first transducer ring 30 with respect to a circumferential position of the second transducer ring 40 will now be described. In this example, an unwrapped planar view of the ultrasonic sensor assembly 10 is shown for illustrative purposes and to more clearly depict the locations of the transmitters 32a-32d with respect to the receivers 42a-42d. In particular, the pipe 12, first transducer ring 30, and second transducer ring 40 are depicted as being two dimensionally planar in FIG. 3 for ease of reference. Further, portions of the pipe 12 from the first end 14 to the first transducer ring 30 and from the second transducer ring 40 to the second end 16 are also not shown so as to more clearly depict the transmitters and receivers. However, in operation, the ultrasonic sensor assembly 10 including the pipe 12 will more closely resemble the structure shown in FIGS. 1 and 2.

To determine the relative position of the first transducer ring 30 and second transducer ring 40, the first transducer ring 30 will initially transmit the waves 50 along the pipe 12 towards the second transducer ring 40. In particular, the waves 50 are transmitted from one or more of the transmitters 32a-32d. In the shown example, the waves 50 are transmitted from the third transmitter 32c, however in operation, the waves 50 could similarly be transmitted from the first transmitter 32a, second transmitter 32b, fourth transmitter 32d, and/or other not shown transmitters.

The third transmitter 32c (or other transmitters) can transmit a plurality of the waves 50, including a first wave 50a, a second wave 50b, a third wave 50c, and a fourth wave 50d. Of course, in further examples, any number of waves can be transmitted, such as greater than or less than the four waves that are shown. These waves 50a-50d can be transmitted simultaneously (i.e., multiple waves transmitted at substantially the same time) or sequentially (i.e., each wave successively transmitted after a preceding wave). As such, the waves 50a-50d represent simultaneous and/or sequential transmission. The waves 50a-50d will propagate through the pipe 12 from the first transducer ring 30 towards the second transducer ring 40.

The waves 50a-50d transmitted by the third transmitter 32c include non-dispersive guided waves. As is generally known, non-dispersive guided waves traveling through the pipe 12 have a substantially constant velocity that is independent of changes in wall thickness of the pipe 12. Likewise, defects in the pipe 12, such as corrosion, voids, inclusions, etc., have a minimal or negligible effect on the velocity of the non-dispersive guided waves through the pipe 12. Accordingly, a time of flight of the waves 50a-50d from the first transducer ring 30 to the second transducer ring 40 depends primarily on the distance from the transmitter (e.g., third transmitter 32c in the shown example) to one of the receivers. The time of flight will therefore be generally independent of changes in wall thickness or defects (e.g., caused by corrosion, voids, inclusions, etc.).

The waves 50a-50d transmitted by the third transmitter 32c are received by one or more of the receivers 42 of the second transducer ring 40. In the shown example, the first receiver 42a receives the first wave 50a, the second receiver 42b receives the second wave 50b, the third receiver 42c receives the third wave 50c, and the fourth receiver 42d receives the fourth wave 50d. Determining the relative position is of course not specifically limited to including the four waves, and instead could include the transmission of more or less waves than as shown. Likewise, the waves 50a-50d are not limited to being transmitted from the third transmitter 32c, and instead could be transmitted from one or more of the first transmitter 32a, second transmitter 32b, fourth transmitter 32d, or other, not shown transmitters. Further still, the receivers 42a-42d are not limited to including the four receivers, and could include a greater or smaller number of receivers than as shown.

Figure 4:
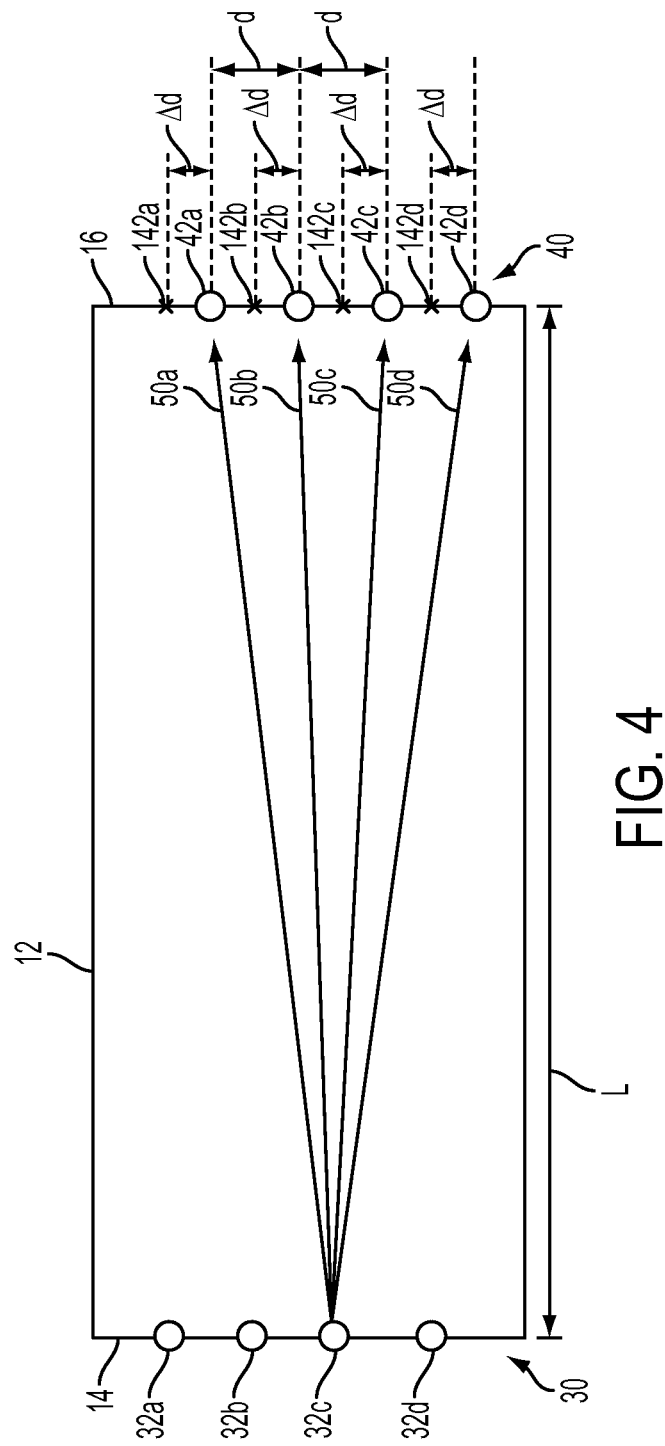
FIG. 4 is an unwrapped planar view of the ultrasonic sensor assembly similar to FIG. 3 during a process of determining a relative position of the first transducer ring with respect to the second transducer ring.

Turning now to FIG. 4, the operation of determining the relative position of the first transducer ring 30 and second transducer ring 40 will further be described. As shown, the transmitters 32 of the first transducer ring 30 are longitudinally misaligned from the receivers 42 of the second transducer ring 40. By being longitudinally misaligned, the transmitters 32 are not located at the same circumferential position as the receivers 42 along the outer surface 18 of the pipe 12. For example, the first receiver 42a is offset (i.e., positioned lower in shown example) than the first transmitter 32a. Likewise, each of the second receiver 42b, third receiver 42c, and fourth receiver 42d are offset (i.e., positioned lower) than the second transmitter 32b, third transmitter 32c, and fourth transmitter 32d, respectively. Of course, in further examples, the transmitters 32 could include a larger or smaller offset from the receivers 42 than as shown.

To determine the relative position, an offset distance of the receivers 42 with respect to a longitudinally aligned positioned will be determined. The longitudinally aligned position includes a location that is longitudinally aligned with one of the transmitters (e.g. first to fourth transmitters 32a-32d) such that an axis from one of the transmitters to the longitudinally aligned position is parallel to a longitudinal axis of the pipe 12. For example, FIG. 4 depicts four longitudinally aligned positions (shown generically/schematically with x's): a first longitudinally aligned position 142a, a second longitudinally aligned position 142b, a third longitudinally aligned position 142c, and a fourth longitudinally aligned position 142d. Each of these longitudinally aligned positions corresponds to (i.e., is longitudinally aligned with) one of the transmitters. In particular, the first longitudinally aligned position 142a is longitudinally aligned with the first transmitter 32a. The second longitudinally aligned position 142b is longitudinally aligned with the second transmitter 32b. The third longitudinally aligned position 142c is longitudinally aligned with the third transmitter 32c. The fourth longitudinally aligned position 142d is longitudinally aligned with the fourth transmitter 32d. Accordingly, a line from the first transmitter 32a to the first longitudinally aligned position 142a will be parallel to the longitudinal axis of the pipe 12. Likewise, a line from each of the second, third, and fourth transmitters 32b-32d to the second, third, and fourth longitudinally aligned positions 142b-142d, respectively, will also be parallel to the longitudinal axis of the pipe 12.

Next, an offset distance, represented as Δd, between each of the longitudinally aligned positions 142a-142d and each of the receivers 42a-42d will be determined. A separation distance, represented as d, is defined as a distance separating each of the receivers 42a-42d. For example, the first receiver 42a is separated from the second receiver 42b by the separation distance d. Likewise, the same separation distance d separates the second receiver 42b from the third receiver 42c, and the third receiver 42c from the fourth receiver 42d. This separation distance d can be readily obtained in any number of ways, such as by measurement, obtaining from a manufacturer of the second transducer ring 40, etc. In one example, this separation distance d can be the same for the receivers 42 in the second transducer ring 40 as with the transmitters 32 in the first transducer ring 30.

To determine the offset distance Δd, a distance from each of the transmitters 32a-32d to the receivers 42a-42d will first be determined. In the shown example, the distance from the third transmitter 32c to each of the receivers 42a-42d is determined by analyzing characteristics of the waves 50a-50d, including time of flight, amplitude, etc. Since the waves 50a-50d include the non-dispersive guided waves that are generally independent of wall thickness, the time of flight for waves 50a-50d traveling a longer distance will be longer as compared to a time of flight for a shorter distance. Further, the velocity of the waves 50a-50d is generally known and constant through the pipe 12. As such, the time of flight of the waves 50a-50d can be measured, such as by the controller 20, for each of the receivers 42a-42d. In particular, the time of flight for the first wave 50a from the third transmitter 32c to the first receiver 42a is measured. Likewise, the time of flight for each of the second wave 50b, third wave 50c, and fourth wave 50d will be measured from the third transmitter 32c to the second receiver 42b, third receiver 42c, and fourth receiver 42d, respectively.

The time of flight of each of the waves 50a-50d can then be used to calculate the distance between the third transmitter 32c and each of the receivers 42a-42d. The velocity for each of the waves 50a-50d is known (and is generally the same). Accordingly, the time of flight (e.g., seconds, milliseconds, etc.) for each of the waves 50a-50d multiplied by the velocity (e.g., distance/seconds or milliseconds) will yield the distance from the third transmitter 32c to each of the receivers 42a-42d. This distance can be represented in the formula below as 32c, 42. For example, a distance from the third transmitter 32c to the first receiver 42a is represented as (32c, 42a). Likewise, distances from the third transmitter 32c to the second receiver 42b, third receiver 42c, and fourth receiver 42d are represented as (32c, 42b), (32c, 42c), and (32c, 42d), respectively.

With the separation distance d and distances between the third transmitter 32c and each of the receivers 42a-42d now known, the relative position of the transmitters 32a-32d with respect to the receivers 42a-42d can now be calculated. Initially, a distance from the third transmitter 32c to the third longitudinally aligned position 142c is shown below. This distance also corresponds to a length of the inspection region 34:

$$32c, 142C = L \tag{1}$$

A formula representing the distance from the third transmitter 32c to the third receiver 42c is shown below (as 32c,

42c) and is based on the Pythagorean Theorem. Here, Δd represents the offset distance between the third longitudinally aligned position 142c and the third receiver 42c while L represents the longitudinal distance from the third transmitter 32c to the third longitudinally aligned position 142c:

$$32c, 42c = \sqrt{\Delta d^2 + L^2} \tag{2}$$

Next, a formula representing the distance from the third transmitter 32c to the fourth receiver 42d is shown below, wherein (d+Δd) represents the offset distance between the third longitudinally aligned position 142c and the fourth receiver 42d. L again represents the longitudinal distance from the third transmitter 32c to the third longitudinally aligned position 142c:

$$32c, 42d = \sqrt{(d+\Delta d)^2 + L^2} \tag{3}$$

A formula representing the distance from the third transmitter 32c to the second receiver 42b is shown below, wherein (d−Δd) represents the offset distance between the third longitudinally aligned position 142c and the second receiver 42b. L again represents the longitudinal distance from the third transmitter 32c to the third longitudinally aligned position 142c:

$$32c, 42b = \sqrt{(d-\Delta d)^2 + L^2} \tag{4}$$

Using formulas (3) and (4), the offset distance Δd can be determined:

$$\Delta d = \frac{(32c, 42d)^2 - (32c, 42b)^2}{4d} \tag{5}$$

Next, the longitudinal distance L between the first transducer ring 30 and the second transducer ring 40 can also be determined:

$$L = \sqrt{(32c, 42c)^2 - \Delta d^2} \tag{6}$$

$$L = \sqrt{(32c, 42c)^2 - \left(\frac{(32c, 42d)^2 - (32c, 42b)^2}{4d}\right)^2} \tag{7}$$

Accordingly, by initially knowing the separation distance d between each of the receivers 42a-42d and the time of flight of each of the waves 50a-50d, the offset distance Δd of the receivers 42a-42d from the longitudinally aligned positions 142a-142d is determinable. Likewise, the longitudinal distance between the first transducer ring 30 and second transducer ring 40, designated as longitudinal distance L, can similarly be calculated.

It is to be appreciated that shown examples and the aforementioned formulas include the waves 50a-50d propagating only from the third transmitter 32c. However, the method of determining the relative position of the first transducer ring 30 with respect to a circumferential position of the second transducer ring 40 is not so limited. Rather, in further examples, any of the transmitters 32 (e.g., first transmitter 32a, second transmitter 32b, fourth transmitter 32d, etc.) could be used instead of the third transmitter 32c. Similarly, the offset distance Δd and longitudinal distance L could be calculated by using greater than or less than the four waves 50. Further still, the formulas are not limited to using the second receiver 42b, third receiver 42c, and fourth receiver 42d. Instead, the formulas are still effective when using the first receiver 42a, some or all of the second, third, and fourth receivers 42b-42d, and/or other, not shown receivers.

By calculating the relative position of the first transducer ring 30 with respect to a circumferential position of the second transducer ring 40, precise alignment of the transducer rings is no longer needed. Further, alignment tools (e.g., mechanical tools, optical/laser alignment tools, software tools, etc.) may no longer be needed to precisely align the transducer rings. Instead, the first transducer ring 30 and second transducer ring 40 could be attached to the pipe 12. Once attached, the aforementioned method can quickly and accurately determine the relative positions of the transducer rings. The first transducer ring 30 and second transducer ring 40 can then be used to accurately determine locations of characteristics (e.g., corrosion, thickness, voids, inclusions, etc.) within the pipe 12.

In a second example, the relative position of the first transducer ring 30 with respect to the circumferential position of the second transducer ring 40 is determinable with a parameter optimization process. Within the parameter optimization process, one or more of the waves 50 are initially transmitted by the transmitters 32. As described above, the waves 50 include non-dispersive guided waves that have a generally constant velocity traveling through the pipe 12. The velocity of the waves 50 is largely independent of pipe thickness variations, presence/absence of corrosion, cracks, etc. In one possible example, the non-dispersive guided waves have a low frequency such that the sensitivity of the velocity of the waves 50 with respect to pipe thickness changes is negligible.

The waves 50 transmitted from the transmitters 32 of the first transducer ring 30 are received by the receivers 42 at the second transducer ring 40. As described above, the characteristics of the waves 50 are inspected, such as with the controller 20, to detect the relative position of the first transducer ring 30 to the second transducer ring 40. For example, the characteristics of the waves 50 include the time of flight between transmitters 32 of the first transducer ring 30 and the receivers 42 of the second transducer ring 40. The time of flight for the waves 50 will be measured for some or all of the combinations of transmitters 32 and receivers 42. For instance, a separate time of flight between the first transmitter 32a and each of the receivers 42 (e.g., first receiver 42a, second receiver 42b, third receiver 42c, fourth receiver 42d, etc.) is measured. Likewise, times of flights for the second transmitter 32b, third transmitter 32c, fourth transmitter 32d and each of the receivers may also be measured.

Next, with these measured times of flights, a model will be created that approximates the relative position of the first transducer ring 30 with respect to a position (e.g., circumferential, axial, etc.) of the second transducer ring 40. The model can be in the form of an equation, formula, or the like, and can incorporate a number of variables in approximating the relative positions of the first transducer ring 30 and second transducer ring 40. Variables can include, for example, time of flight between individual transmitters and receivers, the pipe diameter, nominal pipe wall thickness, spacing between the first transducer ring 30 and second transducer ring 40, etc.

Within this model, an estimated location of the first transducer ring 30 and second transducer ring 40 is determined. This estimated location can be in the form of an XY position of the individual transmitters 32 and receivers 42, the relative location of the transmitters 32 to the receivers 42, or the like. Further, the model may include multiple equations, formulas, etc., such as by having an equation/formula for each combination of transmitters 32 and receivers 42. This equation/formula includes, as a variable, an estimated time of flight between each particular combination of transmitter 32 and receiver 42.

Next, parameter optimization is used to optimize the locations of the first transducer ring 30 with respect to the second transducer ring 40 within the model. In particular, the measured time of flights for each of the waves 50 will be compared to the estimated time of flights generated within the model. For example, the model may generate an estimated time of flight of 150 microseconds between one particular combination of transmitter 32 and receiver 42. In comparison, the measured value of the time of flight between this combination of transmitter 32 and receiver 42 may have been 151 microseconds. As such, an error of 1 microsecond is determined for this particular transmitter/receiver combination. A similar comparison can then be made for each combination of transmitter 32 and receiver 42 (e.g., difference between measured time of flight and model/estimated time of flight).

Next, a sum of square errors is used to calculate the difference between the model and measured values. This sum of square errors is used to determine how closely the model approximates the actual positions of transmitters 32 with respect to the receivers 42. For instance, each of the errors (e.g., difference between measured time of flight and model/ estimated time of flight) for each combination of transmitters 32 and receivers 42 is determined. These errors are then each squared (i.e., multiplying each error by itself) and added together. This summation will generate a figure of merit that indicates how closely the model matches the measurement with respect to the relative positions of the first transducer ring 30 and second transducer ring 40. A lower figure of merit indicates that the model more closely matches the measurements (e.g., measured time of flight) than a higher figure of merit.

By using the parameter optimization process, a relatively accurate determination of the relative positions of the first transducer ring 30 with respect to a position (e.g., circumferential, axial, etc.) position of the second transducer ring 40 is determinable. In particular, a position of the first transducer ring 30 with respect to the second transducer ring 40 is calculated by comparing measured values (e.g., time of flight between transmitters and receivers) with a model of predicted values.

The invention has been described with reference to the example embodiments described above. Modifications and alterations will occur to others upon a reading and understanding of this specification. Example embodiments incorporating one or more aspects of the invention are intended to include all such modifications and alterations insofar as they come within the scope of the appended claims.

What is claimed is:

1. An ultrasonic sensor assembly for testing a pipe, the ultrasonic sensor assembly including:
   a first transducer ring attached to the pipe and operatively configured to transmit a wave along the pipe;
   a second transducer ring attached to the pipe and spaced from the first transducer ring along a length of the pipe and operatively configured to receive the wave transmitted from the first transducer and operatively configured to output a signal indicative of characteristics of the wave from the first transducer ring received by the second transducer ring, the second transducer ring being at a circumferential position relative to a circumferential position of the first transducer ring; and
   a controller operatively connected to the first transducer ring and the second transducer ring and being operatively configured to control the first transducer ring to transmit the wave along the pipe and operatively configured to process the signal from the second transducer ring including determining the relative circumferential position of the first transducer ring with respect to the circumferential position of the second transducer ring, which is a measure of offset circumferential distance of the second transducer ring from longitudinal alignment with the first transducer ring, based on the characteristics of the wave from the first transducer ring received by the second transducer ring.

2. The ultrasonic sensor assembly of claim 1, wherein the characteristics of the wave include a time of flight.

3. The ultrasonic sensor assembly of claim 1, wherein the wave includes one or more non-dispersive guided waves.

4. The ultrasonic sensor assembly of claim 3, wherein the first transducer ring includes a plurality of transmitters, each of the transmitters being configured to transmit the non-dispersive guided waves.

5. The ultrasonic sensor assembly of claim 4, wherein the second transducer ring includes a plurality of receivers, each of the receivers being configured to receive the non-dispersive guided waves.

6. The ultrasonic sensor assembly of claim 5, wherein one of the transmitters is configured to successively transmit the non-dispersive guided waves.

7. The ultrasonic sensor assembly of claim 6, wherein different receivers are configured to receive different non-dispersive guided waves from the transmitter.

8. The ultrasonic sensor assembly of claim 7, wherein a time of flight of the different non-dispersive guided waves is compared to determine the relative position of the first transducer ring with respect to the second transducer ring.

9. The ultrasonic sensor assembly of claim 1, wherein transmitters in the first transducer ring are longitudinally misaligned from receivers in the second transducer ring.

10. An ultrasonic sensor assembly for testing a pipe, the ultrasonic sensor assembly including:
a first transducer ring attached to the pipe, the first transducer ring including a plurality of transmitters for transmitting a plurality of non-dispersive guided waves along the pipe; and
a second transducer ring spaced apart from the first transducer ring along a length of the pipe and attached to the pipe, the second transducer ring including a plurality of receivers for receiving the non-dispersive guided waves from the first transducer ring and operatively configured to output a signal indicative of characteristics of the waves from the plurality of transmitters in the first transducer ring received by the plurality of receivers in the second transducer ring, the second transducer ring being at a circumferential position relative to a circumferential position of the first transducer ring; and
a controller operatively connected to the first transducer ring and the second transducer ring and being operatively configured to control the first transducer ring to transmit the waves along the pipe and operatively configured to process the signal from the second transducer ring including determining the relative circumferential position of the first transducer ring with respect to the circumferential position of the second transducer ring, which is a measure of offset circumferential distance of one of the receivers on the second transducer ring from longitudinal alignment with an associated one of the transmitters on the first transducer ring, based on a comparison of a time of flight of the non-dispersive guided waves from the transmitters in the first transducer ring and received by the receivers in the second transducer ring.

11. The ultrasonic sensor assembly of claim 10, wherein the transmitters extend circumferentially around an outer surface of the pipe, each the transmitters being spaced apart from adjacent transmitters by a separation distance.

12. The ultrasonic sensor assembly of claim 11, wherein the receivers extend circumferentially around an outer surface of the pipe, each of the receivers being spaced apart from adjacent receivers by a separation distance.

13. The ultrasonic sensor assembly of claim 12, wherein one of the transmitters is configured to successively transmit the non-dispersive guided waves to a plurality of the receivers.

14. The ultrasonic sensor assembly of claim 13, wherein the time of flight of non-dispersive guided waves received by each of the receivers from the transmitter are compared to determine the relative position of the first transducer ring with respect to the second transducer ring.

15. The ultrasonic sensor assembly of claim 14, wherein the relative position of the first transducer ring with respect to the second transducer ring includes a circumferential location of the transmitters with respect to the receivers.

16. The ultrasonic sensor assembly of claim 14, wherein the relative position of the first transducer ring with respect to the second transducer ring includes a longitudinal distance between the first transducer ring from the second transducer ring.

17. A method of positioning an ultrasonic sensor assembly on a pipe, the method including the steps of:
attaching a first transducer ring to the pipe;
attaching a second transducer ring to the pipe spaced apart from the first transducer ring along a length of the pipe;
transmitting a wave along the pipe from the first transducer ring to the second transducer ring; and
determining a relative position of the first transducer ring with respect to a circumferential position of the second transducer ring and that is a measure of offset circumferential distance of the second transducer ring from longitudinal alignment with the first transducer ring based on characteristics of the wave received by the second transducer ring.

18. The method of claim 17, wherein the step of determining the relative position of the first transducer ring with respect to the second transducer ring includes analyzing a time of flight of the wave received by the second transducer ring.

19. The method of claim 17, wherein the relative position of the first transducer ring with respect to the second transducer ring includes a circumferential location of transmitters of the first transducer ring with respect to receivers of the second transducer ring.

20. The method of claim 17, wherein the relative position of the first transducer ring with respect to the second transducer ring includes a longitudinal distance between the first transducer ring from the second transducer ring.

* * * * *